United States Patent [19]

Saul

[11] Patent Number: 4,538,607

[45] Date of Patent: Sep. 3, 1985

[54] TRACHEOSTOMY VALVE

[75] Inventor: Aage E. Saul, Karlstad, Sweden

[73] Assignee: AB Fixfabriken, Göteborg, Sweden

[21] Appl. No.: 577,295

[22] Filed: Feb. 6, 1984

[51] Int. Cl.³ .............................................. A61M 16/00
[52] U.S. Cl. .................................... 128/207.16; 623/9
[58] Field of Search ...................... 128/207.16, 207.14; 3/1.3

[56] References Cited

U.S. PATENT DOCUMENTS

| | | | |
|---|---|---|---|
| 3,066,674 | 12/1962 | Capra | 128/207.16 |
| 3,137,299 | 6/1964 | Tabor | 128/207.16 |
| 3,263,684 | 8/1966 | Bolton | 128/207.16 |
| 3,827,440 | 8/1974 | Birch et al. | 128/207.16 |
| 3,844,290 | 10/1974 | Birch et al. | 128/207.16 |
| 4,040,428 | 8/1977 | Clifford | 128/207.16 |
| 4,325,366 | 4/1982 | Tabor | 128/207.16 |

Primary Examiner—Henry J. Recla
Attorney, Agent, or Firm—Hill, Van Santen, Steadman & Simpson

[57] ABSTRACT

A permanent tracheostoma is often necessary in patients with respiratory diseases such as severe bronchial asthma or chronic bronchitis in order to reduce dead space. Another group of patients who require a permanent tracheostoma are those with laryngeal stenoses or bilateral vocal cord pareses whose general condition makes them unsuitable candidates for more advanced surgical procedures.

The invention provides a two-way tracheostoma valve adjustable for either inspiration and expiration or for inspiration only in which case it also serves as a speech valve.

The valve comprises three main elements: a cylindrical housing, a complementary shaped cover, and a disc-like-element disposed within said housing and cover and arranged for displacement therein. The cover has a circular end having an off-center opening forming an air inlet/outlet or inlet only depending on the position of the cover.

16 Claims, 7 Drawing Figures

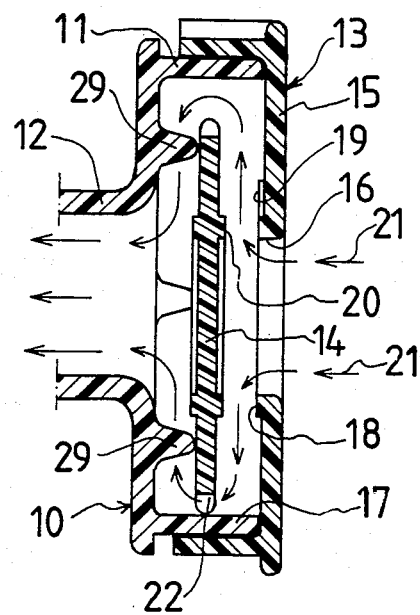
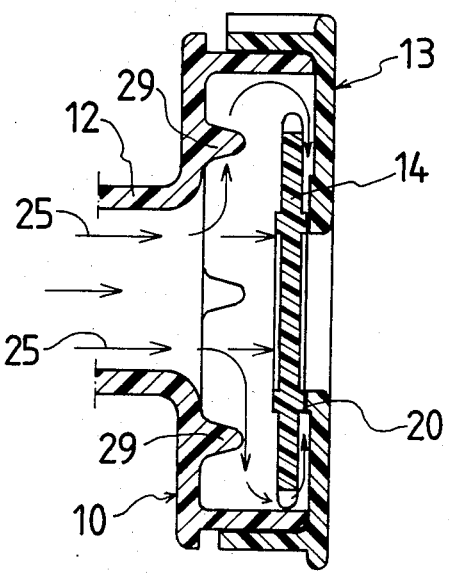
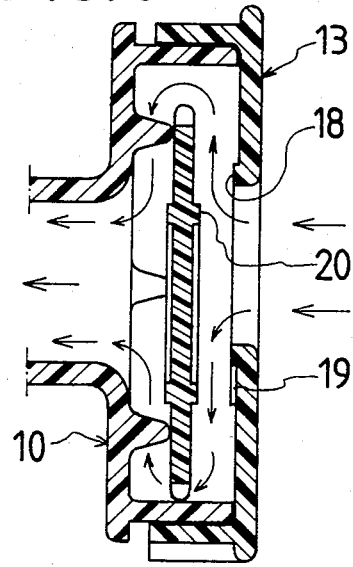
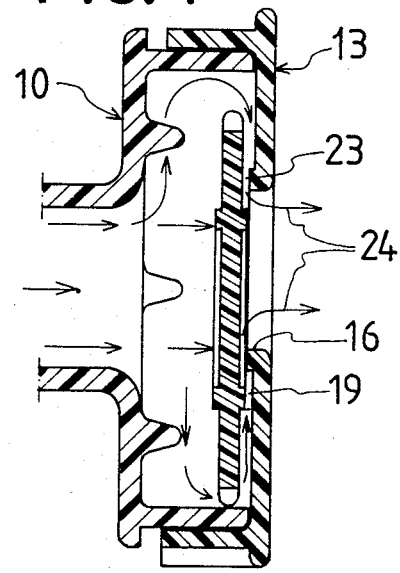

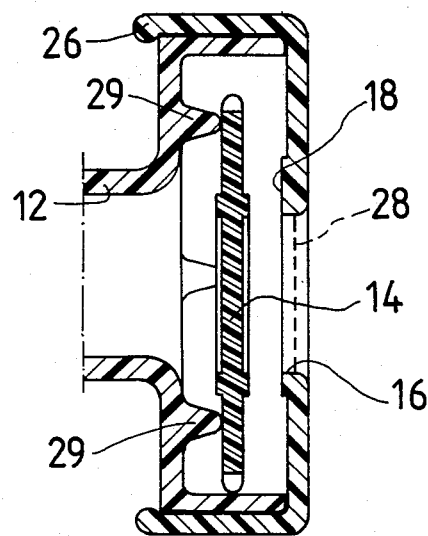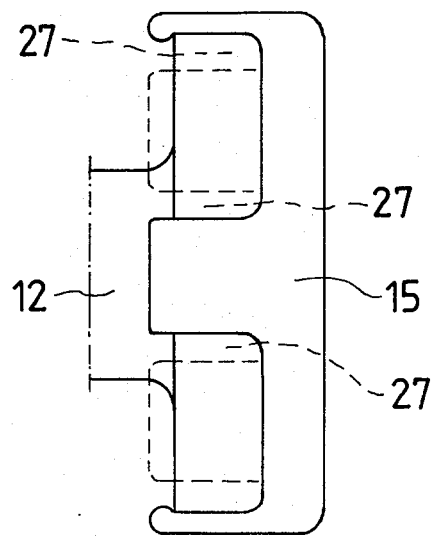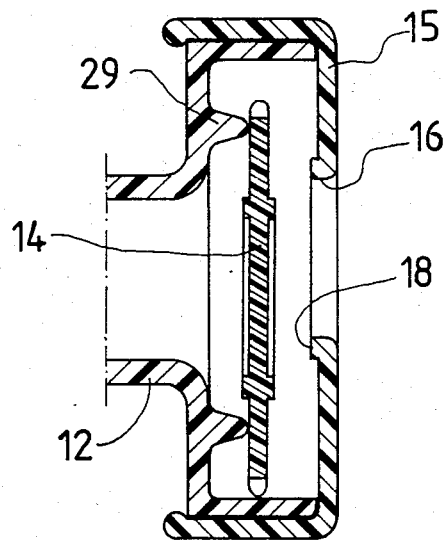

TRACHEOSTOMY VALVE

BACKGROUND OF THE INVENTION

1. Field of the Invention

The present invention relates to tracheostomy valves to be attached to a tube placed in the stoma of a patient.

2. Prior Art

A permanent tracheostoma is sometimes necessary in order to obtain adequate ventilation and to reduce dead space in patients with stenoses of the larynx or the subglottic space. It is also often indicated in cases of respiratory insufficiency due to chronic bronchitis or severe bronchial asthma, and in patients with bilateral vocal cord pareses where a laterofixation cannot be done. This has usually been achieved by the insertion of a conventional tracheostomy tube which, however, carries many problems; the ability to cough is greatly reduced when a sufficient intra-abdominal pressure cannot be acquired, speech is impaired, the tracheostomy tube has to be secured by bands around the neck and it must be changed at regular intervals, etc. The by-passing of the nose creates problems concerning the humidification of the airways.

The drawbacks of the conventional tracheostomy tube technique have encouraged the construction of a permanent tracheal cannula and to-day there are cannulas for permanent use. The cannulas are usually kept in position by an outer flange and four flaps on the tracheal side.

In order to obtain the full benefit of such permanent cannulas there is a need for disposable tracheostomy valves that facilitate speech and coughing and, additionally, prevent dehydration of the airways of the patient.

SUMMARY OF THE INVENTION

The invention provides a special two-way valve adjustable for either inspiration and expiration or for inspiration only in which case it also serves as a speech valve.

In the broadest sense thereof, the invention provides a tracheostomy valve, comprising a housing having means for mounting the housing to a tracheal cannula, a cover placeable onto the housing and adjustable from a first position to at least a second position, a disc-like element within the housing and the cover are arranged for displacement therein, an air inlet/outlet formed in the cover and closeable at least partially by said disc, air-passage-forming-means on said housing for permanent communication between the tracheal cannula and the interior space formed by the housing and the cover, and means for closing said inlet/outlet in the outlet mode thereof by said disc in the first position of the housing and for allowing a controlled air flow in said second position.

In the most preferred practical embodiment, the housing is provided with a cylindrical portion to be closed by a complementary shaped cover having an off-center opening in a circular member forming one end of the cover.

The means for closing said inlet/outlet comprises a circumferential valve seat formed around the opening on the side of the cover facing the interior of the valve and a complementary ledge on the disc.

Preferably, the valve seat is provided with abutment means for forming a tight seal between the ledge of the disc and the cover in the first position of the cover, and for allowing controlled ventilation in the second position of the cover.

Advantageously, the abutment means comprises a further ledge of generally uniform radial width surrounding said inlet/outlet.

Alternatively, the abutment means comprises a further ledge, a portion of which has a reduced radial width.

Said portion may be formed as at least one notch-shaped region of said circumferential valve seat.

The design of said further ledge may be such that the radial width thereof provides a gradually increased outflow of air when rotating said housing.

In the case where the housing and cover are cylindrical, the adjustment between speech valve function and controlled inspiration/expiration function is obtained by simply rotating the cover.

The elements of the valve are preferably injection molded from plastic and for reducing sound level during operation of the valve, the disc-like-element preferably is manufactured from a relatively softer material than the rest of the valve.

BRIEF DESCRIPTION OF THE DRAWINGS

FIG. 1 shows the inspiration phase, of a valve operated as a speech valve according to the invention, FIG. 2 shows the same valve during the expiration phase, FIG. 3 shows the inspiration phase of a valve operable both for inspiration and expiration, FIG. 4 shows the valve in FIG. 3 during expiration, FIG. 5 shows a valve having a modified cover, FIG. 6 shows the cover in FIG. 5 having slots formed in the cylindrical surface thereof, and FIG. 7 shows a valve having a valve seat ledge of uniform radial width on the inside of the inlet/outlet opening in the cover.

DESCRIPTION OF PREFERRED EMBODIMENTS

The valve in FIG. 1 has a housing 10 having a cylindrical collar 11. A connection piece 12 to be inserted into a permanent tracheostomy tube (not shown) is formed integral with the rest of the housing. The housing as well as a cover 13 and a disc like valve membrane 14 are preferably injection molded from plastic, for instance from PTFE. In order to reduce the sound level during operation, the membrane 14 preferably is manufactured from a softer material than the rest of the valve elements.

The cover 13 is pushed onto the collar 11 and maintained in place by friction in the FIG. 1 embodiment. However, the cover is easily rotatable relative to the housing by simply gripping the cover by the fingers. The cover has a plane circular element 15 having an off-center hole delimited by a marginal edge 16 and forming the air inlet/outlet of the valve.

The disc element 14 has an effective cross section less than the internal diameter of the collar 11, and basically the disc 14 is guided by the "lower" portion 17 of the collar when displacement thereof is effected by difference in pressure on the respective sides of the disc.

In the operative position, when the connection piece 12 is mounted to the tracheostomy tube, the valve disc basically assumes such a position that it rides on the surface portion 17.

A circumferential valve seat 18 extends around the edge 16 of the opening and is facing the interior of the housing and cover. In the embodiment according to FIG. 1, there is a void space 19 formed in a region of the valve seat 18 having an extended dimension in the radial direction of the arrangement.

The effective valve seat portion 18 faces a complementary shaped ledge 20 on the disc 14. By the term "complementary" is meant an arrangement that effectively blocks all air passage when contacting, in register, the effective valve seat 18. In the position shown in FIG. 1, the off-center hole delimited by the marginal edge 16 is in register with the ledge 20, meaning that the effective valve 18 seat also faces the ledge 20 such that the two sealing elements are in register, but spaced apart, in the actual direction of the valve movement.

In FIG. 1 there is a free passage of air into the interior of the housing/cover, as indicated by the arrows 21. The housing is provided with projections 29 forming air passage means for permanent communication between the tracheostomy cannula (not shown) and the interior space formed by the housing and the cover. The disc has circumferentially spaced notches 22 allowing passage of air also at the "rest" region (bottom region) 17 of the housing.

Thus, in FIG. 1 there is a free passage of air into the tracheostomy tube.

In FIG. 2, the valve acts as a check valve preventing passage of air, meaning that the valve is operating as a speech valve. The air pressure from the patient, indicated by the arrows 25 moves the disc into sealing engagement with the cover. As the valves seat 18 is in register with the ledge 20, there will be a pressure induced air tight seal between the disc 14 and the cover 15.

In FIG. 3, the cover 13 has been rotated 180°. The effective valve seat 18 and the ledge 20 are no longer in register (when the disc assumes its operative "vertical position"). However, the flow of air into the valve and out to the tracheostomy tube is almost the same as in FIG. 1.

But, when the pressure of the disc originates from the air in the tracheostomy tube, during the expiration phase, the disc assumes the position in FIG. 4. The void space 19 and the slot 23 allow a controlled amount of air 24 to flow out through the valve while the rest of the air flows through the airways of the patient for humidifying said ways. This function is the one for instance taking place during sleep.

The slot 23 is formed due to the eccentric mutual position between the ledge 20 and the margin 16 of the inlet/outlet opening in the cover.

In FIG. 5 the valve seat 18 has a continuously, or gradually possibly with some discontinuities, varying radial width. Such construction provides a gradually increasing through flow area of the slot 23 (during the expiration phase) when rotating the cover. The degree of humidification of the airways may thus be adjusted very simply by a suitable rotation of the cover. In order to increase the attachment force acting between the cover and housing, the cover in FIG. 5 is terminated by a bead or hook type end portion 26. Such attachment may for instance be necessary for allowing short term pressure increases on the patient side of the valve, for instance when coughing. For facilitating the mounting of the valve, there for instance may be arranged slots 27, in the collar 11.

In all embodiments of the valve according to the invention there may also be provided a grid structure 28 (FIG. 5) acting as a filter for separation of minor objects, for instance flies, during the inspiration phase.

FIG. 7, finally, just shows valve seat version 18 of constant radial width. The off-center (eccentric) placement of the inlet/outlet defined by the margin 16 still provides for the necessary air passage slot 23 (FIG. 4) when rotating the cover.

I claim:
1. A tracheostomy valve, comprising
   a housing having an open first end and an opposite second end, means for mounting the opposite second end of the housing to a tracheal cannula,
   a cover movably mounted on the housing over said open first end to define a chamber therebetween and adjustable from a first position to at least a second position,
   a disc-like-element within the housing and cover and arranged for reciprocation therebetween,
   an air inlet/outlet formed in the cover communicating said chamber with the surrounding atmosphere, said cover including means wherein said inlet/outlet is closed by said disc in the first position of the cover and for allowing a controlled air flow in said second position,
   said mounting means including air-passage-forming-means on said housing for permanent communication between the tracheal cannula and said chamber formed by the housing and the cover.
2. A valve according to claim 1, said housing having a cylindrical portion, said cover having a complemental shape receptive of said cylindrical portion, and said cover having a circular member forming one end thereof, said circular member having an off-center opening therein.
3. A valve according to claim 2, said closing means including an annular valve seat formed around said opening on the side of said cover facing the interior of said housing, and said disc-like element having a ledge complemental to said valve set.
4. A valve according to claim 3, said valve seat having abutment means for enabling a tight seal between said ledge and said valve seat in said first position, and for enabling controlled ventillation in said second position.
5. A valve according to claim 19, said abutment means comprising a further ledge of generally uniform radial width surrounding said inlet/outlet.
6. A valve according to claim 4, said abutment means comprising a further ledge, a portion of which having reduced radial width.
7. A valve according to claim 6, said portion of said further ledge being at least one notch-shaped region of said valve seat.
8. A tracheostomy valve, comprising:
   a housing having an open first end and an opposite second end, means for mounting the opposite second end of the housing to a tracheal cannula, said second end provided with a cylindrical portion, a complementary shaped cover rotatably mounted over said first end to define a chamber with said housing, said cover being rotatable from a first position to a rotated position between the first position and 180° and having an off center air inlet/outlet opening in a circular member forming one end of the cover communicating the chamber with the surrounding atmosphere, disc-like-element within the housing and cover and arranged for reciprocation therebetween, said mounting means including air passage forming means on said housing for permanent communication between the tracheal cannula and the chamber formed by the housing and the cover, and means for closing said inlet/outlet including an annular valve seat formed around the opening on the side of the cover facing the chamber and a complementary ledge on the disc in alignment with said valve seat when said cover is in said first position, said valve seat being provided with abutment means for forming a tight seal between the ledge and the cover in said first position of the cover and for allowing a controlled ventilation in a rotated position of the cover.

9. A valve as in claim 8, wherein said abutment means comprises a further ledge surrounding said outlet.

10. A valve as in claim 9, wherein said further ledge has at least one portion of reduced radial width.

11. A valve as in claim 9, wherein said further ledge has a radial width providing gradually increasing outflow of air when rotating said cover.

12. A valve as in claim 8, wherein said disc like element is manufactured from a relatively softer material than the rest of the valve.

13. A valve as in claim 8, wherein said disc-like element is provided with notches at the marginal edge thereof.

14. A valve as in claim 8, wherein said cylindrical portion of said cover is terminated by a hook type end portion gripping said housing.

15. A valve as in claim 14, wherein said cylindrical portion is provided with slots.

16. A valve as in claim 8, wherein said inlet/outlet is provided with a grid structure.

* * * * *